United States Patent [19]

Dankowski et al.

[11] Patent Number: 5,654,269
[45] Date of Patent: Aug. 5, 1997

[54] ACTIVATORS FOR INORGANIC PEROXO COMPOUNDS AND AGENTS CONTAINING THEM

[75] Inventors: Manfred Dankowski, Moembris; Michael Del Grosso, Freigericht; Astrid Dorfer, Gruendau, all of Germany

[73] Assignee: Degussa Aktiengesellschaft, Frankfurt am Main, Germany

[21] Appl. No.: 487,432

[22] Filed: Jun. 7, 1995

[30] Foreign Application Priority Data

Aug. 25, 1994 [DE] Germany ............... 44 29 943.526

[51] Int. Cl.$^6$ ............... C11D 3/39; C11D 3/395; C11D 7/38; C09K 3/00
[52] U.S. Cl. ............... 510/313; 252/186.38; 252/186.39
[58] Field of Search ............... 252/186.38, 186.39; 510/312, 313

[56] References Cited

U.S. PATENT DOCUMENTS

| | | | |
|---|---|---|---|
| 3,655,567 | 4/1972 | Gray | 510/376 |
| 3,840,466 | 10/1974 | Gray | 510/306 |
| 3,928,223 | 12/1975 | Murray | 510/313 |
| 4,179,390 | 12/1979 | Spadini et al. | 510/295 |
| 4,399,049 | 8/1983 | Gray et al. | 510/301 |
| 4,412,934 | 11/1983 | Chung et al. | 252/186.38 |
| 5,405,413 | 4/1995 | Willey et al. | 8/111 |
| 5,518,650 | 5/1996 | Jaekel et al. | 252/186.39 |

FOREIGN PATENT DOCUMENTS

| | | |
|---|---|---|
| 2038106 | 2/1972 | Germany. |
| 1949561 | 10/1977 | Germany. |
| 855735 | 12/1960 | United Kingdom. |

Primary Examiner—Joseph D. Anthony

[57] ABSTRACT

A and N-acyl compounds are used for the activation of inorganic peroxo compounds in washing, bleaching and cleaning agents and disinfectants. Compounds of formula (I)

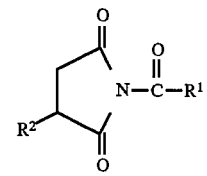

wherein $R^1$ represents a $C_6$ to $C_{10}$ alkyl group; and $R^2$ represents hydrogen or selected substituents, are highly effective activators for aqueous bleaching, washing, cleaning and disinfecting liquors. A particularly preferred activator is N-n-nonanoylsuccinimide.

14 Claims, No Drawings

ACTIVATORS FOR INORGANIC PEROXO COMPOUNDS AND AGENTS CONTAINING THEM

INTRODUCTION AND BACKGROUND

The present invention relates to the use of N-alkanoyl compounds as activators for hydrogen peroxide and for inorganic peroxo compounds which are sources of hydrogen peroxide and capable of releasing it in aqueous phase, wherein the activation consists in the formation of an organic percarboxylic acid. In a further aspect, the present invention relates to these new activators and their use in washing, bleaching and cleaning agents as well as disinfectant compositions containing inorganic peroxo compounds.

Inorganic peroxygen compounds are used as oxidizing agents in bleaching, washing and cleaning agents and disinfectants in order to improve the action of such agents. Hydrogen peroxide and such substances as release hydrogen peroxide in aqueous solution, such as perborates and percarbonates, in particular are used as peroxygen compounds. The action of the inorganic peroxygen compounds depends on the pH value and considerably on the temperature. While at temperatures above about 80° C. a good effect is achieved, it is known that at lower temperatures, especially at or below about 60° C. or at or below about 40° C., the co-utilization of so-called activators is required with the named inorganic peroxygen compounds. The activators are principally N-acyl or O-acyl compounds. In aqueous phase percarboxylic acids, which display a good washing, cleaning, bleaching and disinfecting action in the low-temperature range also, are formed out of $H_2O_2$ or $H_2O_2$-releasing inorganic peroxygen compounds and the activators.

Among the N-acyl compounds, numerous classes of substances have been proposed in the past as activators, including N,N,N',N'-tetraacetylethylenediamine (TAED), N,N,N', N'-tetraacetylglycoluril (TAGU), N-($C_1$ to $C_4$)- or N-($C_6$ to $C_{10}$)-alkanoylhydantoins (DE-C 19 49 561 and U.S. Pat. No. 4,412,934 respectively), N,N'-($C_1$ to $C_8$)-alkanoyl-2,5-diketopiperazines (DE-A 20 38 106) and N-($C_1$ to $C_4$)-alkanoylsuccinimide (DE-C 19 49 561 and GB-B 855735). Despite this variety of proposed activators, of the N-acyl compounds previously disclosed essentially only TAED has been successful on the market.

From U.S. Pat. No. 4,412,934 bleaching agent compositions are known that contain as the activator, substances of the formula R—CO—L, wherein R is an alkyl group with 5 to 18 C atoms, whose longest chain R—CO has 6 to 10 carbon atoms, and the conjugate acid of the leaving group L has a $pK_a$ value of 6 to 13. Among the leaving groups, many groups linked to R—CO via oxygen but also a few via amide nitrogen are disclosed, including the N-hydantoinyl group, but not the N-succinyl group. Preferred leaving groups are phenol derivatives; the group R preferably represents linear ($C_5$ to $C_9$)-alkyl chains; the activator nonanoyloxybenzenesulphonate (NOBS) is particularly preferred. NOBS is a very active activator, contained in conventional commercial bleaching agent compositions, whose bleaching effect exceeds that of TAED.

In view of the growing demand for washing, bleaching and cleaning agents and disinfectants for the low-temperature range, there is an interest in further activators based on N-acyl compounds, which come up to or exceed the property characteristics of NOBS. The activators should as far as possible be accessible from easily available raw materials and be readily biodegradable.

SUMMARY OF THE INVENTION

An object of the invention is to improve the low temperature performance of washing, bleaching and cleaning agents and disinfectants.

Another object of the invention is to devise formulations for the above purpose that are convenient to manufacture and do not adversely impact the environment. In achieving the above and other objects, one feature of the invention resides in the use of N-alkanoyl compounds of the formula (I),

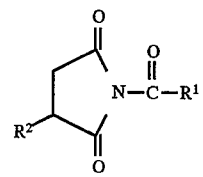

wherein $R^1$ represents a $C_6$ to $C_{10}$ alkyl group, and $R^2$ represents hydrogen, an HOOC— or $HO_3S$— group or a salt thereof, a $C_1$ to $C_4$ alkyl group or a hydroxyl group, as activator for hydrogen peroxide and inorganic peroxo compounds that are sources of hydrogen peroxide and capable of releasing it in aqueous bleaching, washing, cleaning and disinfecting liquids.

In carrying out the present invention, in the aqueous bleaching, washing, cleaning and disinfecting liquids, the pH value is adjusted to greater than 4 up to 13, preferably to 8 to 11 and, a percarboxylic acid with 7 to 11 C atoms, active in bleaching and disinfection, is formed by perhydrolysis of the activator of formula (I). Peroxo-n-nonanoic acid is particularly active, so that the use of activators of formula (I) with $R^1$ equal to n-octyl is preferred. Activators with $R^2$ equal to hydrogen are also preferred because of their easy manufacture from readily available materials.

DETAILED DESCRIPTION OF THE INVENTION

The method according to the present invention relates to the activation of $H_2O_2$ and such inorganic peroxygen compounds that release hydrogen peroxide in the aqueous phase especially perborates, in particular sodium perborate monohydrate and sodium perborate tetrahydrate, superoxidized sodium perborate and sodium percarbonate ($2Na_2CO_3 \cdot 3H_2O_2$). Perphosphates, persilicates and persulphates can also be used. Several inorganic peroxo compounds can also be present during the activation. These compounds are well known in the art.

0.05 to 1 moles, preferably 0.1 to 0.5 moles, of activator of formula (I) are used for activation per equivalent of active oxygen of the hydrogen peroxide present and releasable from the inorganic peroxo compounds.

The activators to be used according to the invention can be used for activation in pure form or with auxiliary substances, such as granulating auxiliaries, stabilizers, and pH-regulating substances; suitable forms of addition are powders, pastes, tablets, granules or coated granules.

Activators to be used according to the invention are obtainable by conventional acylation of succinimide which is represented by the structural formula:

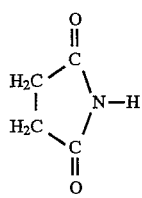

Alternatively, they may be obtained by acylation of succinimide monosubstituted according to formula (I), such as malimide, 2-methylsuccinimide, 2-carboxysuccinimide or 2-sulphosuccinimide, with the required alkanoyl halide with 7 to 11 C atoms, such as nonanoyl chloride. While N-alkanoylsuccinimides with 1 to 5 as well as 12 and 18 C atoms in the alkanoyl groups have been described, the activators according to the invention, such as the particularly preferred nonanoylsuccinimide, are new substances.

The activators and peroxygen compounds can be used according to the invention both in purely aqueous phase and in aqueous-organic phase. A purely aqueous phase is present in the conventional washing, bleaching and cleaning liquors. An aqueous-organic medium can be suitable in disinfectant applications as well as for industrial oxidation processes. The pH value of the reaction medium can range from about 4 and 13, but processes are preferably operated in the alkaline range, usually at pH 8 to 11, since in this range not only the in-situ formation of the organic peracid proceed well but also the stability of the peroxo compounds is satisfactory.

A further provision of the invention is directed to bleaching, washing and cleaning agents and disinfectants that contain an inorganic peroxo compound and an activator selected from the group consisting of N-acylated succinimides and N-acylated monosubstituted succinimides of the previously mentioned formula I that are usable according to the invention. N-n-nonanoylsuccinimide is preferred as activator in these agents. The agents again contain the substances mentioned previously, in particular sodium perborates and sodium percarbonate, as inorganic peroxo compound. The agents contains 0.05 to 1 moles, preferably 0.1 to 0.5 moles, of activator of formula (I) per equivalent of active oxygen from the inorganic peroxo compound or compounds.

The agents can contain one or more inorganic peroxygen compounds as well as one or more activators, including at least one according to the invention and also conventional commercial or other previously known activators as required.

Activators to be used according to the invention and inorganic peroxygen compounds can be combined with all conventional ingredients of washing and bleaching agents in order to obtain washing and bleaching agents which are suitable for textile treatment in the low- and medium-temperature ranges, but also for washing at the boil.

The main constituents of such washing and bleaching agents, aside from the peroxo compounds and activators mentioned, are builders and surfactants. Among the builders, in particular sodium aluminum silicates (zeolites), phyllosilicates, condensed phosphates, alkali metal silicates, alkali metal carbonates, complexing aminocarboxylic acids, polyphosphonic acids, multivalent hydroxycarboxylic acids as well as polycarboxylic acids and salts of the acids have to be mentioned. To be mentioned, especially among the surfactants are nonionic surfactants, such as polyethylene glycol ethers of fatty alcohols and of alkylphenols as well as long-chain alkylglycosides, and anionic surfactants, such as alkylbenzenesulphonates and sulphates of fatty alcohols and polyethyleneglycol monoethers. Other substances in the washing and bleaching agents are electrolytes, pH-regulating substances, stabilizers, foam regulators, anti-redeposition agents, optical brighteners, enzymes and finishing agents. The substances and amounts to be used in such agents are known to the expert - H. G. Hauthal provides a review together with literature in "Chemie in unserer Zeit" 26 (1992) Nr. 6, 293–303).

Washing and bleaching agents according to the invention generally have the following composition:

| | |
|---|---|
| 5 to 30 wt %, | preferably 10 to 25 wt %, anionic and/or nonionic surfactants, |
| 5 to 60 wt %, | preferably 20 to 40 wt %, builders selected from the group consisting of sodium aluminum silicates, condensed phosphates, alkali metal silicates, alkali metal carbonates and mixtures thereof, |
| 0 to 20 wt %, | preferably 1 to 8 wt %, builders selected from the group consisting of complexing aminocarboxylic acids, polyphosphonic acids, polycarboxylic acids or their salts as well as mixtures thereof, |
| 2 to 35 wt %, | preferably 10 to 25 wt %, inorganic peroxo compounds selected from the group consisting of sodium perborates and sodium percarbonate, |
| 0.3 to 20 wt %, | preferably 1 to 10 wt %, of N-alkanoylsuccinimide compounds of formula (I) to be used according to the invention as activators to 100 wt % conventional auxiliary substances and water. |

Pure bleaching agents, such as can be used as additives for washing agents free of bleaching agents, generally have the following composition:

| | |
|---|---|
| 5 to 50 wt %, | in particular 15 to 35 wt %, inorganic peroxygen compounds, in particular sodium borate monohydrate or tetrahydrate or/and sodium percarbonate, |
| 2 to 50 wt %, | in particular 5 to 25 wt %, N-alkanoylsuccinimide compounds of formula (I) to be used according to the invention as activators, |
| 0 to 5 wt % | peroxide stabilizers, such as water glass and complexing agents, |
| 0 to 40 wt % | pH-regulating agents, |
| to 100 wt % | other conventional auxiliary substances. |

Cleaning agents according to the invention usually contain surfactants, builders, peroxidated compounds and activators to be used according to the invention; scouring agents contain in addition constituents with abrasive action.

Disinfectants according to the invention are based in general on a combination of inorganic peroxo compounds and activators to be used according to the invention as well as auxiliary substances selected from the group consisting of stabilizers, surfactants, pH-regulating substances and, optionally, organic solvents and microbiocidal substances other than the percarboxylic acids formed from the activators and peroxo compounds.

It has been established that the activator effect of the activators, based on N-acyl compounds, to be used according to the invention sharply exceeds that of previously known N-acyl compounds, such as the TAED put on the market. Unexpectedly, the activator effect also does not merely approach that of the previously most effective activator NOBS, but surpasses it. The outstanding effect of the activators of formula (I) and of N-n-nonanoylsuccinimide in particular was surprising since N-alkanoylsuccinimides with few C atoms in the alkanoyl group have already been described as activators in the prior art. Measured by delta diffuse reflection increase (%) after washing in the Launder-o-meter under US washing conditions at 30° C. and equal dosages by weight of the activators, the effect of N-n-nonanoylsuccinimide is higher by a factor of about 2.3 than that of N-acetylsuccinimide, which is not according to the invention. The effectiveness as activators of TAED and NOBS is furthermore evident from the following table. The washing agent compositions used for the test and the concentrations of use thereof are to be taken from example 2.

TABLE 1

| Activator | Delta diffuse reflection increase (%)* | |
|---|---|---|
| | Mean value** | Ketchup |
| N-n-nonanoylsuccinimide | 1.7 | 2.3 |
| N-acetylsuccinimide | 0.7 | −0.3 |
| TAED | 0.4 | −1.5 |
| NOBS | 1.4 | 1.0 |
| without activator | 0.0 | 0.0 |

*Delta diffuse reflection increase (%) is obtained by subtracting the diffuse reflection increase for washing agents free from activator and bleaching agent from the diffuse reflection increase for washing agents containing activator and bleaching agent.
**Mean value from 9 test strains in each case with coffee, tea, red wine, paprika, ketchup and curry.

The unusual effect of the activator according to the invention compared with NOBS in the bleaching of tomato ketchup stains also is evident from the preceding table.

The peracid release from activators according to the invention and sodium perborate is retarded compared with N-acetylsuccinimide and compared with NOBS, which can be advantageous with regard to the preservation of the activity of the enzymes which the washing agent possibly contains.

EXAMPLE 1

N-Nonanoylsuccinimide 20 g succinimide were suspended in 100 ml pyridine, 0.5 g N,N-dimethylaminopyridine added, and 39.2 g nonanoic acid chloride added dropwise at ice-bath temperature. Subsequently the mixture was stirred for 1 h at room temperature and 500 ml of 2N HCl solution were added with cooling. The aqueous phase was extracted with ethyl acetate and the organic phase washed with 2N HCl solution and dried ($Na_2SO_4$). After removing the solvent, the residue was twice recrystallized from n-hexane. 31.6 g (65%) N-nonanoylsuccinimide were obtained as a colourless solid. Melting point: 59 to 60° C. (n-hexane). The $^1$H-NMR spectroscopic data are in agreement with the structure.

EXAMPLE 2

Investigation of the activator effect of nonanoylsuccinimide by comparison with the activators not according to the invention, N-acetylsuccinimide, TAED and NOBS,

| | |
|---|---|
| Washing appliance: | Launder-o-meter |
| Washing temperature: | 30° C. |
| Water hardness: | 5° d |
| Washing programme: | 500 ml washing tank |
| | 200 ml washing liquor |
| | 15 min washing time |
| Liquor ratio: | 3 × 30 sec rinsing time |
| | 1:20 |
| Dosing: | 1.35 g/l, equal to 0.27 g/wash cycle, of a washing agent, commercially available in the USA and free of bleaching agent and activator (containing anionic surfactants, zeolite A, sodium citrate, sodium sulphate, sodium silicate, soda and enzymes) 0.015 g each of sodium perborate monohydrate and activator per wash cycle. |
| Test fabric: | cotton |
| Test stains: | coffee, wfk 10K; tea wfk CFT BC-1; paprika wfk 10 N; curry wfk CFT BC-4; red wine EMPA 114; tomato ketchup wfk 10 T. |

After the washing of the test fabric, the diffuse reflection increase is measured in each case and compared with the diffuse reflection increase obtained by means of washing agent free of activator and bleaching agent (=delta remission). The values on which the diffuse reflection increase is based are mean values from nine of the same soilings.

The results follow from Table 1, which has already been described previously.

EXAMPLE 3

Peracid release by n-nonanoylsuccinimide in comparison with that by N-acetylsuccinimide.

8 g/l of washing agent free from bleaching agent and activator, 1.5 g/l sodium perborate monohydrate and 0.5 g/l activator were weighed into water at 30° C. and the formation of pernonanoic acid or peracetic acid determined as a function of time.

The following table shows the peracid equivalent after time t based on 1 mole of activator.

TABLE 2

| | Equivalents period | |
|---|---|---|
| Time (min) | N-nonanoylsuccinimide | N-acetylsuccinimide |
| 2 | 0.54 | 1.0 |
| 6 | 0.81 | 1.0 |
| 10 | 0.87 | 1.0 |
| 15 | 0.89 | 0.99 |
| 20 | 0.90 | 0.98 |
| 30 | 0.92 | 0.95 |

EXAMPLE 4

Activator effect of N-n-Nonanoylsuccinimide and NOBS at 30° C. in the presence of sodium perborate and an enzyme-containing washing agent.

Cotton test fabric with blood staining (wfk CFT CS1) was washed. Washing appliance, washing temperature, wash programme and liquor ratio according to Example 2; water hardness 14° d.
Dosage:
Compact washing agent: 3.8 g/l=0.76 g/wash cycle
Washing agent recipe in g/l liquor:

| Washing agent constituents in g/l liquor | |
| --- | --- |
| Alkylbenzenesulphonates | 0.52 |
| Fatty alcohol ethoxylates | 0.35 |
| Soap | 0.10 |
| Zeolite A | 1.52 |
| Polycarboxylates | 0.18 |
| Soda | 0.76 |
| Na and Mg silicates | 0.24 |
| CMC | 0.06 |
| Auxiliary substances (total) | 0.07 |
| | 3.8 g/l |

Enzymes: 0.085 g/l=0.0171 g/wash cycle protease (Savinase of the Novo company).
Bleaching agent: 0.144 g/wash cycle sodium borate monohydrate (SPM).
Activator:

a) 0.125 g/wash cycle N-n-Nonanoylsuccinimide b) 0.144 g/wash cycle NOBS

The dosage of the activators was equal to that of the peracids:

$O_a$ from $H_2O_2$, 76 mg/l in each case; $O_a$ from peracid (calculated) each 33 mg/l.

After the wash, the diffuse reflection increase was measured:

TABLE 3

| | Diffuse reflection increase (%) |
| --- | --- |
| a) N-n Nonanoylsuccinimide + SPM | 8.9 |
| b) NOBS + SPM | 8.1 |

Comparison shows that the activator according to the invention surpasses the previously known activator.

Further modifications and variations of the foregoing will be apparent to those skilled in the art and are intended to be encompassed by the claims appended hereto.

German priority application P 44 30 071.9 is relied on and incorporated herein by reference.

We claim:

1. A method for improving the low temperature performance of aqueous bleaching, washing, cleaning and disinfecting liquors comprising adding thereto an N-alkanoyl activator compound of the formula (I),

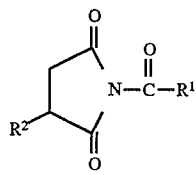

wherein $R^1$ represents a $C_8$ alkyl group and $R^2$ is hydrogen, an HOOC— or $HO_3S$— group or a salt thereof, a $C_2$ to $C_4$ alkyl group or a hydroxyl group, said compound being an activator for hydrogen peroxide and inorganic peroxo compounds releasing hydrogen peroxide contained in said liquors.

2. The method according to claim 1, wherein said liquors are in a predominantly aqueous solution at a pH value between 8 and 11.

3. The method according to claim 1, wherein sodium perborate or sodium percarbonate is present in solution as the inorganic peroxo compound.

4. The method according to claim 1 wherein 0.05 to 1 moles, per equivalent of active oxygen from hydrogen peroxide or from the inorganic peroxo compound, of an activator of formula (I) is present.

5. The method according to claim 1 wherein 0.1 to 0.5 moles, per equivalent of active oxygen from hydrogen peroxide or from the inorganic peroxo compound, of an activator of formula (I) is present.

6. The method according to claim 1 wherein 0.05 to 1 moles, per equivalent of active oxygen from hydrogen peroxide or from the inorganic peroxo compound, of an activator of formula (I) wherein $R^1$ is equal to n-octyl and $R^2$=H, is present.

7. The method according to claim 1 wherein said activator is in the form of powder, paste, tablet, granule or coated granule.

8. The method according to claim 1 wherein $R^2$ is H.

9. An oxidizing, bleaching or cleaning agent or disinfectant comprising (a) an inorganic peroxo compound releasing hydrogen peroxide in the presence of water and (b) an activator based on an N-alkanoyl compound, having the formula (I)

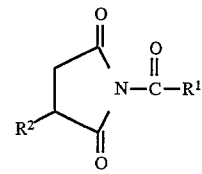

wherein $R^1$ represents a $C_8$ alkyl group and $R^2$ is hydrogen, an HOOC— or $HO_3S$— group or a salt thereof, a $C_2$ to $C_4$ alkyl group or a hydroxyl group, said compound being an activator for hydrogen peroxide and inorganic peroxo compounds releasing hydrogen peroxide contained in said liquors.

10. The composition according to claim 9, containing 0.05 to 1 moles, of the activator of formula (I) per mole of inorganic peroxo compound.

11. The composition according to claim 9, containing 0.1 to 0.5 moles, of the activator of formula (I) per mole of inorganic peroxo compound.

12. The composition according to claim 9 wherein said inorganic peroxo compound is a member selected from the group consisting of sodium perborate monohydrate, sodium perborate tetrahydrate, superoxidized sodium perborate and sodium percarbonate.

13. A washing and bleaching agent according to claim 9, comprising:

| | |
| --- | --- |
| 2–35 wt % | inorganic peroxo compound |
| 0.2–20 wt % | activator of formula (I) |
| 5–30 wt % | anionic and/or nonionic surfactants |
| 5–60 wt % | inorganic builders |
| 0–20 wt % | organic builders |
| to 100 wt % | conventional auxiliary substances and water. |

14. A bleaching additive according to claim 9 comprising:

| | |
| --- | --- |
| 5–50 wt % | inorganic peroxo compound |
| 2–30 wt % | activator of formula (I) |
| 0–5 wt % | peroxide stabilizers |
| 0–40 wt % | pH-regulating agents |
| to 100 wt % | conventional auxiliary substances and water. |

* * * * *